United States Patent [19]

Baudry et al.

[11] Patent Number: 5,180,400
[45] Date of Patent: Jan. 19, 1993

[54] METHOD FOR DYEING KERATINOUS FIBRES USING AN AMINOINDOLE IN COMBINATION WITH A QUINONE DERIVATIVE

[75] Inventors: Alain Baudry, Gonesse; Alex Junino, Livry-Gargan; Hervé Richard, Paris, all of France

[73] Assignee: L'Oreal, Paris, France

[21] Appl. No.: 707,056

[22] Filed: May 29, 1991

[30] Foreign Application Priority Data

May 29, 1990 [FR] France ............................. 90 06660

[51] Int. Cl.⁵ .............................................. A61K 7/13
[52] U.S. Cl. ............................................ 8/405; 8/406; 8/407; 8/408; 8/423; 8/429; 552/293
[58] Field of Search ................... 8/405, 406, 407, 408, 8/423, 429; 552/293

[56] References Cited

U.S. PATENT DOCUMENTS 4,888,025 12/1989 Bugaut et al. ........................... 8/405
5,053,053 10/1991 De Labbey et al. .................... 8/405

FOREIGN PATENT DOCUMENTS 0376776 7/1990 European Pat. Off. .
2626173 7/1989 France .

Primary Examiner—A. Lionel Clingman
Assistant Examiner—William S. Parks
Attorney, Agent, or Firm—Cushman, Darby & Cushman

[57] ABSTRACT

Method for dyeing keratinous fibres, characterized in that at least one composition (A) containing at least one aminoindole in a medium appropriate for dyeing is applied to these fibres, the application of the composition (A) being preceded or followed by the application of a composition (B) containing, in a medium appropriate for dyeing, at least one quinone derivative chosen from ortho- or para-benzoquinones, ortho- or para-benzoquinone monoimines or diimines, 1,2- or 1,4-naphthoquinones, ortho- or para-benzoquinone sulphonimides, α,ω-alkylene-bis-1,4-benzoquinones, or 1,2- or 1,4-naphthoquinone monoimines or diimines, the aminoindoles and the quinone derivatives being chosen such that the difference in redox potential ΔE between the redox potential $E_i$ of the aminoindoles, determined at pH 7 in a phosphate medium on a vitreous carbon electrode by voltametry, and the redox potential $E_q$ of the quinone derivative, determined at pH 7 in a phosphate medium by polarography on a mercury electrode relative to the saturated calomel electrode, in such that $$\Delta E = E_i - E_q \leq 470 \ mV.$$

17 Claims, No Drawings

METHOD FOR DYEING KERATINOUS FIBRES USING AN AMINOINDOLE IN COMBINATION WITH A QUINONE DERIVATIVE

The present invention relates to a new method for dyeing keratinous fibres and more particularly human keratinous fibres, such as hair, using at least one aminoindole in combination with at least one quinone derivative.

The dyeing of keratinous fibres and in particular hair using 5,6-dihydroxyindole or its derivatives has already been described, in particular in the French Patents FR-A-1,133,594, 1,166,172 and 2,390,158.

The Patent Applications 2,536,993 and 2,594,331 propose dyeing methods using 5,6-dihydroxyindole and using either metal cations acting as a melanogenesis promoter or manganese in the form of permanganate, or dichromate. Moreover, in its patents FR-A 2,593,061 and 2,593,062, the Applicant has described a dyeing method using 5,6-dihydroxyindole in combination with iodide ions, these methods requiring the use of hydrogen peroxide.

The Application EP-A 271,186 relates to methods for dyeing hair using hydroxyindole derivatives in combination with oxidising systems such as periodic acid and its water-soluble salts, silver oxide or lead oxide, Fenton's reagent, caesium sulphate, ammonium persulphate, sodium hypochlorite, ferric chloride or potassium ferricyanide.

The Applicant has discovered, and it is this that is the subject of the invention, that it is possible, surprisingly, to carry out dyeing with the aid of an aminoindole by impregnating the keratinous fibres, and in particular the hair, with the aminoindole, this impregnation being preceded or followed by the application of a composition containing a quinone derivative as oxidising agent.

The Applicant has discovered, in particular, that it is possible to dye natural hair in shades ranging from light chestnut to black.

The subject of the invention is, therefore, a new method for dyeing keratinous fibres, and in particular human keratinous fibres, using an aminoindole and, as oxidising agent, a quinone derivative.

Other subjects of the invention are multicompartment devices used within the framework of this method.

Other subjects of the invention will become apparent on reading the description and the examples which follow.

The method for dyeing keratinous fibres and in particular human keratinous fibres, such as hair, according to the invention, is essentially characterised in that at least one composition (A) containing at least one aminoindole in a medium appropriate for dyeing is applied to these fibres, the application of the composition (A) being preceded or followed by the application of a composition (B) containing, in a medium appropriate for dyeing, at least one quinone derivative chosen from ortho- or para-benzoquinones, ortho- or para-benzoquinone monoimines or diimines, ortho- or para-benzoquinone sulphonimides, α,ω-alkylene-bis-1,4-benzoquinones, 1,2-or 1,4-naphthoquinones and 1,2- or 1,4-naphthoquinone monoimines or diimines; the aminoindoles and the quinone derivatives being chosen such that the difference in redox potential $\Delta E$ between the redox potential $E_i$ of the aminoindoles, determined at pH 7 in a phosphate medium on a vitreous carbon electrode by voltametry, and the redox potential $E_q$ of the quinone derivatives, determined at pH 7 in a phosphate medium by polarography on a mercury electrode and relative to the saturated calomel electrode, is such that $$\Delta E = E_i - E_q \leq 470 \text{ mV}.$$

The aminoindoles used according to the invention correspond to the following formula (1):

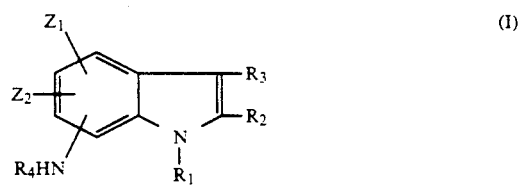

in which:

$R_1$ denotes a hydrogen atom or a straight-chain or branched $C_1$-$C_4$ alkyl group;

$R_2$ and $R_3$, independently of one another, denote a hydrogen atom, a $C_1$-$C_4$ alkyl group, a carboxyl group or a ($C_1$-$C_4$) alkoxycarbonyl group;

$R_4$ denotes a hydrogen atom or a $C_1$-$C_4$ alkyl or $C_1$-$C_4$ hydroxyalkyl or $C_2$-$C_4$ polyhydroxyalkyl or acetyl group or a $C_1$-$C_6$ aminoalkyl group in which the amine may optionally be monosubstituted or disubstituted by a $C_1$-$C_4$ alkyl;

$Z_1$ and $Z_2$, which may be identical or different, represent a hydrogen atom, a $C_1$-$C_4$ alkyl group, a hydroxyl, a halogen or $C_1$-$C_4$ alkoxy;

the $R_4NH$ group occupying the 4, 5, 6 or 7 positions of the benzene ring, and their salts.

The compounds of formula (I) in which R is other than a hydrogen atom are denoted by the formula (IA) and may be prepared by the reaction scheme below.

The compound (IA) is obtained from the compound (IB) ($R_4=H$) by the methods for substitition of aromatic amines in accordance with the following reaction scheme:

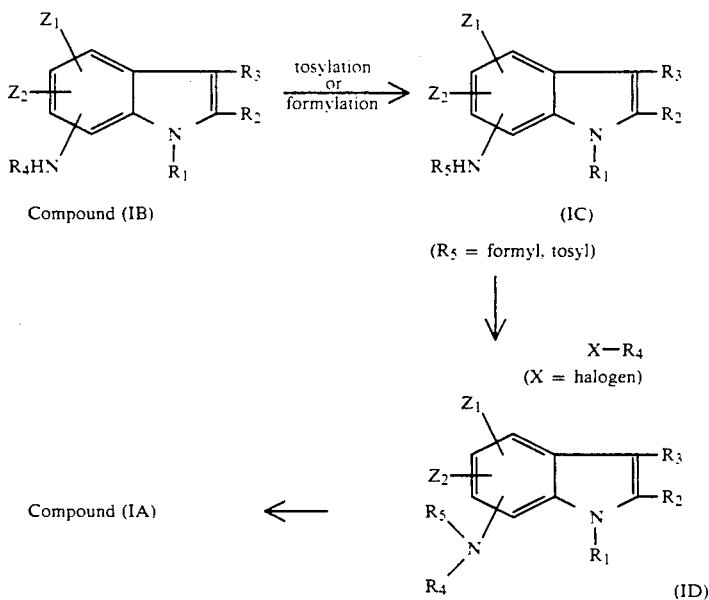

Compound (IB)

(IC)

($R_5$ = formyl, tosyl)

$X-R_4$
(X = halogen)

Compound (IA)

(ID)

The compound (IC) is obtained by formylation or tosylation. The compound (IC) is alkylated in a second step using alkyl halide $X-R_4$. When the alkyl halide is used in excess, a second group $R_4$ is introduced. The product (IA) is obtained by deformylation or detosylation of the compound (ID).

Amongst the hydroxyalkyation methods, the following may be mentioned, for example: the action of β-chloroethyl chloroformate on the compound (IB), which enables, in a first step, the corresponding β-chloroethyl carbamate to be obtained, which, subjected in a second step to the action of a strong inorganic base, enables the compound (IA) in which the radical $R_4$ is a β-hydroxyethyl radical to be obtained.

The particularly preferred compounds according to the invention are chosen from: 5-aminoindole, 6-aminoindole, 7-aminoindole, 6-N-β-hydroxyethylaminoindole, 6-N-β-hydroxyethylamino-1-methylindole, 6-methylaminoindole, 6-amino-N-methylindole, 6-amino-2-carboxyindole, 4-amino-2,3-dimethylindole,6-amino-2,3-dimethylindole,7-amino-2,3-dimethylindole, 6-amino-3-ethyl-2-methylindole, 7-amino-3-ethyl-2-methylindole,6-amino-3-methylindole,6-amino-2-methylindole and 6-amino-2-ethoxycarbonylindole, 4-aminoindole, 5-amino-6-methoxy-2,3-dimethylindole, 6-amino-5-methoxy-2,3-dimethylindole, 5-amino-6-hydroxy-2,3-dimethylindole, 6-amino-5-hydroxy-2,3-dimethylindole, 5-amino-N-methylindole, 6-N-(β,γ-dihydroxypropyl)aminoindole, 6-amino-2,3,4,5-tetramethylindole, 6-amino-5-chloro-2,3-dimethylindole, 6-amino-5-ethyl-2,3-dimethylindole, 6-amino-2,3,4-trimethylindole, 6-amino-5-hydroxy-2-methylindole, 2,3,7-trimethylindole, 6-amino-2,3,5-trimethylindole,
amino-6-methoxy-2,3-dimethylindole, 6-amino-4-methylindole, 6-amino-5-methylindole, 4-amino-7-methylindole, 6-amino-7-ethyl-3-methylindole, 6-amino-5,7-dimethylindole, 6-amino-5,7-diethylindole, 7-amino-5-methyl-2-ethoxycarbonylindole, 7-amino-5-chloro-2-ethoxycarbonylindole, 7-amino-5-ethoxy-2-ethoxycarbonylindole, 7-amino-5-methoxy-2-ethoxycarbonylindole, 7-(4'-dimethyl-amino-1,-methylbutyl)amino-5-methoxyindole, 7-(4,-dimethylaminobutyl)amino-5-methoxyindole, 6-amino-5-fluoroindole, 6-amino-5-fluoro-1-sec-butylindole, 6-amino-5-fluoro-1-n-propylindole, 6-amino-2-methoxycarbonyl-5-methoxy-N-methylindole, 6-amino-5-methoxy-2-methoxycarbonylindole, 6-amino-5-methoxy-2-ethoxycarbonylindole, 6-amino-5-methoxy-2-carboxyindole, 6-amino-5-hydroxy-1,2-dimethylindole and 6-amino-4-methoxy-2-methoxycarbonylindole.

The quinone derivatives are more particularly chosen from the compounds corresponding to the formulae (II) and (II'):

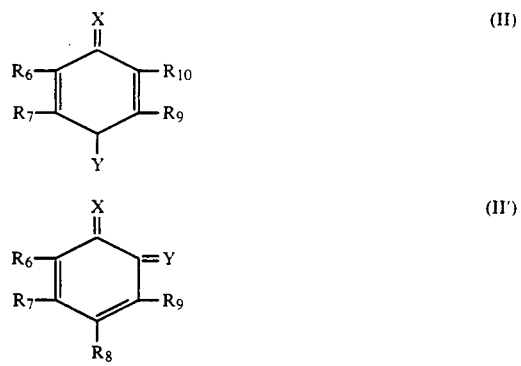

in which formulae:

X denotes oxygen or an $NR_{11}$ group;

Y denotes oxygen or an $NR_{12}$ group;

$R_{11}$ and $R_{12}$, which may be identical or different, denoting hydrogen, halogen, a $C_1$-$C_4$ alkyl or $C_1$-$C_4$ hydroxyalkyl radical, a ($C_1$-$C_4$) alkylsulphonyl radical or a phenylsulphonyl radical; and $R_6$, $R_7$, $R_8$, $R_9$ and $R_{10}$ denote, independently of one another, hydrogen, a ($C_1$-$C_4$) alkyl radical, a carboxyl, ($C_1C_4$) alkylcarbonyl, ($C_1$-$C_4$) alkoxycarbonyl, ($C_1$-$C_4$) alkoxymethyl, ($C_1$-$C_4$) alkylthiomethyl, ($C_1$-$C_4$) hydroxyalkylthiomethyl or ($C_1$-$C_4$) hydroxyalkylsulphinyl group,

(r and r' denoting, independently of one another, hydrogen or $C_1$-$C_4$ alkyl), $C_1$-$C_4$ carboxyalkyl, halogen, hydroxy($C_1$-$C_4$)alkyl, amino which is unsubstituted or substituted by one or two $C_1$-$C_4$ alkyl or hydroxyalkyl, ($C_2$-$C_6$) acylamino or $SO_3M$ groups, where M denotes hydrogen, K or Na, an optionally substituted sulphoxide, sulphone or sulphonamide group, or a radical $OZ_1$ in which $Z_1$ may be hydrogen, ($C_1$-$C_4$) alkyl, ($C_1$-$C_4$) hydroxyalkyl, ($C_1$-$C_4$) carboxyalkyl, or phenyl which is optionally substituted by $C_1$-$C_4$ alkoxy, or a radical —$SZ_2$ in which $Z_2$ is a $C_1$-$C_4$ alkyl, $C_1$-$C_4$ hydroxyalkyl, $C_2$-$C_4$ dihydroxyalkyl or $C_1$-$C_4$ carboxyalkyl group;

it being possible for $R_6$ and $R_7$ to form, with the carbon atoms to which they are attached, the following cyclic group: in which:

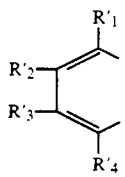

in which:

$R'_1$, $R'_2$, $R'_3$ and $R'_4$ have the meanings indicated above for $R_6$, $R_7$, $R_8$, $R_9$ and $R_{10}$ when they do not form rings.

According to the invention, halogen is preferably chosen from fluorine, chlorine or bromine.

The preferred compounds are chosen from the quinone derivatives for which the potential $E_q$ is higher than or equal to $-220$ mV, and in particular from the benzoquinones of formulae (II) and (II,) in which:

$R_6$, $R_7$, $R_8$, $R_9$ and $R_{10}$ denote, independently of one another, hydrogen, $C_1$-$C_4$ lower alkyl, $C_1$-$C_4$ lower alkoxy, halogen, $C_2$-$C_6$ acylamino, $SO_3M$, ($C_1$-$C_4$)alkoxymethyl, carboxy($C_1$-$C_4$)alkyl, alkoxy($C_1$-$C_4$)carbonyl, di($C_1$-$C_4$)alkylamino, $OZ_1$ in which $Z_1$ represents carboxy($C_1$-$C_4$)alkyl or hydroxy($C_1$-$C_4$)alkyl, or $SZ_2$ in which $Z_2$ represents ($C_1$-$C_4$)alkyl, hydroxy($C_1$-$C_4$)alkyl, dihydroxy($C_2$-$C_4$)alkyl or carboxy($C_1$-$C_4$)alkyl;

X denotes oxygen or the $NR_{11}$ group;

Y denotes oxygen or the $NR_{12}$ group, and $R_{11}$ and $R_{12}$, independently of one another, denote hydrogen, halogen or $C_1$-$C_4$ lower alkyl; methylsulphonyl or phenylsulphonyl.

Other preferred compounds used according to the invention correspond to the formulae (V) and (VI) below:

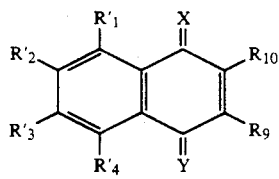

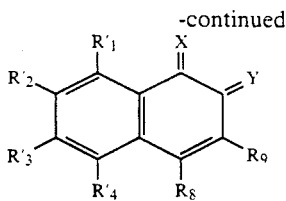

in which formulae:

$R_8$, $R_9$ and $R_{10}$ have the meanings indicated above for the compounds of formulae (II) and (II,); $R'_1$, $R'_2$, $R'_3$ and $R'_4$ having the preferred meanings of $R_6$, $R_7$, $R_8$, $R_9$ and $R_{10}$; and X and Y having the same meanings as those indicated above.

The particularly preferred compounds are chosen from those in which $R'_1$, $R'_2$, $R'_3$, $R'_4$, $R'_8$, $R_9$ and $R_{10}$ denote hydrogen, $C_1$-$C_4$ alkyl, $C_1$-$C_4$ alkoxy, halogen, ($C_2$-$C_6$) acylamino or $SO_3H$.

Amongst these preferred compounds, the following may be mentioned:
1,4-benzoquinone
2-methoxy-1,4-benzoquinone
2-methyl-1,4-benzoquinone
2,6-dimethyl-1,4-benzoquinone
2,3,5-trichloro-6-methyl-1,4-benzoquinone
2-acetylamino-1,4-benzoquinone
2-acetylamino-3,5-dimethyl-1,4-benzoquinone
2-chloro-1,4-benzoquinone
tetrachloro-1,2-benzoquinone
2,3-dimethoxy 1,4-benzoquinone
2-β-carboxyethoxy-1,4-benzoquinone
2-methoxymethyl-1,4-benzoquinone
2-hydroxymethyl-1,4-benzoquinone
2-β-hydroxyethylthio-1,4-benzoquinone
2,5-bis-β-hydroxyethylthio-1,4-benzoquinone
2-β,γ-dihydroxypropylthio-1,4-benzoquinone
2-β-carboxyethylthio-1,4-benzoquinone
2-carboxymethyl-1,4-benzoquinone
2-β-hydroxyethylthio-6-methyl-1,4-benzoquinone
2-methoxycarbonyl-3-methoxy-1,4-benzoquinone
2-methoxycarbonyl-1,4-benzoquinone
2-methylthio-1,4-benzoquinone
2-dimethylamino-1,4-benzoquinone
2-acetylamino-5-methoxy-1,4-benzoquinone
2-(β-hydroxyethylthio)methyl-1,4-benzoquinone
2-(methylthio)methyl-1,4-benzoquinone
4,5-dimethoxy-1,2-benzoquinone
4-methyl-5-chloro-1,2-benzoquinone
4,5-dimethyl-1,2-benzoquinone
2,3-dimethyl-1,4-benzoquinone
2-β-hydroxyethoxy-1,4-benzoquinone
N-methylsulphonyl-1,4-benzoquinone monoimine
N-phenylsulphonyl-1,4-benzoquinone monoimine
1,4-naphthoquinone
1,2-naphthoquinone
1,2-naphthoquinone-4-sulphonic acid
2,3-dichloro-1,4-naphthoquinone and
N-2,6-trichloro-1,4-benzoquinone imine.

Under the customary conditions for dyeing, that is to say for application times of 2 to 30 minutes and a temperature usually tolerated by the models, for example of between 25° and 40° C., the concentration of aminoindole used in the composition (A) is preferably between 0.01 and 0.3 mole/liter.

The concentration of quinone derivative is such that it permits the oxidation of the aminoindole under the conditions customarily used for hairdressing during dyeing and it is preferably between 0.005 and 1 mole/liter in the composition (B).

The pH of the composition (A) is preferably between 2 and 10.

The pH of the composition (B) is preferably between 2 and 10, but this composition is preferably used at an acidic pH.

The compositions (A) and (B) may be made up in the forms customarily used, especially in the dyeing of hair, in particular in the form of a lotion thickened to a greater or lesser extent, a gel or an emulsion, each of which may optionally be packaged as an aerosol.

The medium appropriate for dyeing is generally an aqueous medium which may consist of water or a mixture of water and a solvent, which must be cosmetically acceptable when the composition is applied to hair.

Solvents of this type are chosen more particularly from the organic solvents, such as $C_1$-$C_6$ lower alcohols, such as ethyl alcohol, propyl or isopropyl alcohol, tert-butyl alcohol, ethylene glycol, propylene glycol, ethylene glycol monomethyl, monoethyl or monobutyl ethers, ethylene glycol monoethyl ether acetate, propylene glycol monomethyl ether and dipropylene glycol monomethyl ether and methyl lactate.

The solvents particularly preferred are ethyl alcohol and propylene glycol.

When they are used, the solvents are used more particularly in concentrations of between 10 and 50% in the case of the lower alcohols and in the case of high concentrations of aminoindole.

The compositions (A) and (B) according to the invention may also be stored in an anhydrous solvent medium. The solvents are chosen from the solvents defined above. A medium containing less than 1% of water is termed an anhydrous medium.

When they are used for dyeing hair, the compositions according to the invention may also contain any other adjuvants customarily used in cosmetics, and more particularly anionic, cationic, nonionic or amphoteric surfactants or their mixtures, thickeners, perfumes, sequestrant agents, film-forming agents, treatment agents, dispersing agents, conditioners, preservatives, opacifying agents and agents for swelling keratinous fibres.

The compositions (A) and/or (B) which can be used in the method according to the invention may contain other dyes customarily used for dyeing keratinous fibres, and in particular direct dyes, such as nitrobenzene derivatives, oxidation dyes of the para or ortho type and couplers or so-called "rapid" oxidation dyes, that is to say molecules having a benzene structure, dye precursors able to generate coloured compounds by simple oxidation in air during the time of application to hair, which is generally less than 1 hour, and in the absence of any other oxidising agents.

These compositions may also contain quinone dyes of the class of benzoquinones, benzoquinone imines or benzoquinone diimines, naphthoquinones, naphthoquinone imines or naphthoquinone diimines which do not comply with the potential conditions defined above. These dyes are, in this case, used to impart their inherent shade to the dyeing.

With a view to the implementation of the method according to the invention, the various compositions may be packaged in a multicompartment device, also termed a "kit" or dyeing set, containing all of the components intended to be applied for a single dyeing to the keratinous fibres and in particular the hair, in successive applications with or without premixing.

Devices of this type may comprise a first compartment containing the composition (A) and a second compartment containing the composition (B). Another variant may also consist in storing the composition (A) and/or the composition (B) in an anhydrous solvent medium and in providing a third compartment containing an aqueous medium appropriate for dyeing and cosmetically acceptable if the compositions are intended to be applied to hair. In this case, the contents of the third compartment are mixed just before use in one or other or both of the two compartments containing the anhydrous compositions (A) and/or (B).

The method according to the invention is preferably carried out by applying the composition (A) in a first step and the composition (B) in a second step. It may be used in particular for dyeing natural or already dyed human hair, which may or may not have been permanent-waved or straightened, or highly or slightly bleached hair which may have been permanent-waved.

In this case, the composition (A) is applied at a temperature which can be tolerated by the head, that is to say of between 25° and 40° C., for 2 to 30 minutes and this application is followed, with or without intermediate rinsing, by the application of the composition (B) containing the quinone derivative, which is kept in contact with the hair for 5 to 30 minutes, the dyeing temperature likewise being between 25° and 40° C.

The method according to the invention may also be carried out with a view to tinting or freshening a dyeing which has already been carried out with the aid of aminoindoles, by applying the composition (B) several hours or days after the dyeing with the aid of aminoindoles.

It is also possible to use this method for dyeing fur or wool under the customary industrial conditions in respect of temperature, contact time and concentration.

The examples which follow serve to illustrate the dyeing method according to the invention, without, however, having a limiting character.

PREPARATION EXAMPLE 1

Preparation of 6-N-β-hydroxyethylaminoindole

Step 1

Preparation of 6-N-(β-chloroethoxycarbonyl)aminoindole 0.05 mol (6.6 g) of 6-aminoindole and 5.5 g of calcium carbonate in 30 ml of dioxane are heated to reflux. 0.055 mol (7.9 g) of β-chloroethyl chloroformate is added little by little. The reaction mixture is diluted with ice. The expected product precipitates. It melts at 134° C.

The analysis of the product recrystallised from ethanol gives the following results:

| | Analysis for $C_{11}H_{11}N_2O_2Cl$ | | | | |
|---|---|---|---|---|---|
| | C | H | Cl | O | N |
| Calculated | 55.36 | 4.65 | 14.85 | 13.41 | 11.74 |
| Found | 55.40 | 4.68 | 14.72 | 13.27 | 11.67 |

Step 2

Preparation of 6-N-β-hydroxyethylaminoindole 0.28 mol (66.5 g) of 6-N-(β-chloroethoxycarbonyl)aminoindole is added to 200 ml of 4N sodium hydroxide solution and 66.5 ml of ethanol. The reaction mixture is refluxed for 1 hour. The expected product is precipitated by adding ice. It melts at 99° C.

Elementary analysis of the product obtained gives the following results:

| | Analysis for $C_{10}H_{12}N_2O$ | | | |
|---|---|---|---|---|
| | C | H | N | O |
| Calculated | 68.16 | 6.86 | 15.90 | 9.08 |
| Found | 67.88 | 6.91 | 15.91 | 9.15 |

PREPARATION EXAMPLE 2

Preparation of 6-N-($\beta,\gamma$-dihydroxypropyl)aminoindole 26.4 g of 6-aminoindole are dissolved in 70 ml of absolute alcohol. 29.6 g of glycidol are added and the mixture is stirred for 4 hours at 30°–40° C. The mixture is poured into 200 g of ice-water and extracted with three times 100 ml of ethyl acetate. The solvent is washed with water. It is dried over $Na_2SO_4$ and evaporated to dryness under vacuum.

The oily residue is taken up three times in 0.6 liter of isopropyl ether under reflux. The ether is filtered and evaporated to dryness under vacuum; the residual oil is taken up in 10 cc of ethyl acetate and purified on a silica column (eluent ethyl acetate/heptane 9/1).

The fraction containing the expected product is evaporated to dryness under vacuum.

PREPARATION EXAMPLE 3

Synthesis of 4-Methyl 6-Aminoindole

1) Synthesis of 2,3-Dimethyl-5-Nitroaniline 363 g of 2,3-xylidine are poured into 1.8 liters of pure sulphuric acid keeping the temperature at 40° C. A sulphonitric mixture (132 ml of nitric acid (d = 1.52) and 180 ml of pure sulphuric acid) is added dropwise in the course of 1 hour to this solution, which has been cooled to 12° C., the temperature not rising above 15° C. After 15 minutes, the mixture is poured onto 6 kg of ice, with stirring.

The beige sulphate precipitate is drained and washed twice with 0.5 liter of water and then with three times 0.5 liter of acetone. The paste is mixed to a paste with 0.5 liter of acetone and the paste is rendered alkaline with ammonia and then diluted with 1.5 liters of ice-water. The yellow precipitate is drained, washed with water and then dried. A yellow solid is obtained which has the following characteristics:

| | Elemental analysis for $C_8H_{10}N_2O_2$ | | | |
|---|---|---|---|---|
| | C | H | N | O |
| Calculated | 57.83 | 6.02 | 16.87 | 19.28 |
| Found | 57.91 | 6.03 | 16.78 | 19.20 |

Synthesis of Methyl N-(2,3-Dimethyl-5-Nitrophenyl)Formimidate 66.4 g of 2,3-dimethyl-5-nitroaniline, 0.4 liter of trimethyl orthoformate and 1.6 g of paratoluenesulphonic acid are mixed and the mixture is refluxed for 3 hours.

The mixture is poured onto 1 kg of ice and the precipitate is drained and then washed with twice 0.5 liter of water. The precipitate is redissolved in 0.2 liter of ethyl acetate and the solution is filtered hot. The solid obtained after cooling is filtered off, washed with petroleum ether and dried.

Crystallisation from isopropyl ether leads to white crystals having the following characteristics:

| | Elemental analysis for $C_{10}H_{12}N_2O_3$ | | | |
|---|---|---|---|---|
| | C | H | N | O |
| Calculated | 57.69 | 5.81 | 13.45 | 23.05 |
| Found | 57.74 | 5.84 | 13.39 | 23.25 |

Synthesis of 4-Methyl-6-Nitroindole

A solution of 31 g of potassium ethoxylate, 51 ml of ethyl oxalate and 0.25 liter of dimethylformamide is added to a solution of methyl N-(2,3-dimethyl-5-nitrophenyl)-formimidate (52 g) in 0.37 liter of dimethylformamide. The temperature of the mixture is brought to 40° C. for 3 hours. The precipitate is drained and washed with water. The precipitate is taken up in hot isopropyl ether and the mixture is then filtered.

The filtrate is evaporated and then subjected to chromatography on silica (eluent: heptane/ethyl acetate 9/1). A yellow solid is obtained which has the following characteristics:

| | Elemental analysis for $C_9H_8N_2O_2$ | | | |
|---|---|---|---|---|
| | C | H | N | O |
| Calculated | 61.36 | 4.58 | 15.90 | 18.16 |
| Found | 61.30 | 4.58 | 15.88 | 18.20 |

4) Synthesis of 4-Methyl-6-Aminoindole 4.3 g of the nitro derivative prepared in step 3, 20 ml of ethanol, 9 ml of cyclohexene, 3 ml of water and 2.2 g of 10% palladium-on-charcoal are mixed and the mixture is then refluxed for 2 hours.

The mixture is filtered hot, the catalyst is washed with alcohol and the filtrate is evaporated under vacuum. The precipitate is taken up in isopropyl ether and the mixture is treated with vegetable charcoal and then filtered through celite.

After evaporation of the filtrate, a beige solid is obtained which has the following characteristics:

| | Elemental analysis for $C_8H_{10}N_2$ | | |
|---|---|---|---|
| | C | H | N |
| Calculated | 73.97 | 6.85 | 19.18 |
| Found | 73.84 | 6.99 | 19.06 |

PREPARATION EXAMPLE 4

Synthesis of 4-Amino-7-Methylindole

The same reduction method as in point 4 of Example 3 is used, using 4-nitro-7-methylindole instead of 4-methyl-6-nitroindole.

A pale yellow solid is obtained which has the following characteristics:

| | Elemental analysis for $C_8H_{10}N_2$ | | |
|---|---|---|---|
| | C | H | N |
| Calculated | 73.97 | 6.85 | 19.18 |
| Found | 73.95 | 6.94 | 19.11 |

PREPARATION EXAMPLE 5

A mixture of 0.5 liter of 96° ethanol, 0.5 liter of glacial acetic acid and 100 g of pure iron reduced with hydrogen is brought to 90° C. 51 g of 3-methyl-6-nitro-7-ethylindole are added in portions in the course of 15 minutes.

After 2 hours at 95° C., the ferric sludge is filtered off and the filtrate is cooled and diluted with 3 volumes of water. The mixture is extracted with three times 0.5 liter of ethyl acetate and the organic phases are washed, dried and evaporated. The residue is taken up in ethyl acetate and the mixture is treated with vegetable charcoal, and filtered and the filtrate is cooled.

The light beige precipitate is filtered off and washed with ethyl acetate. The solid is dissolved in 0.1 liter of water, the solution is rendered alkaline with ammonia and an oil precipitates and then solidifies. The precipitate is filtered off, then washed until neutral and then dried. A white solid is obtained which has the following characteristics:

| | Elemental analysis for $C_{11}H_{14}N_2$ | | |
|---|---|---|---|
| | C | H | N |
| Calculated | 75.82 | 8.10 | 16.08 |
| Found | 76.01 | 8.10 | 16.06 |

Examples of Dyeing Methods

EXAMPLE 1

A lock of 1 g of natural hair which is 90% white is impregnated with 5 ml of a 2.5% solution of 6-aminoindole in an aqueous-ethanolic medium (80/20) for 15 minutes.

The lock is rinsed with running water and wrung dry. This lock is impregnated again using 5 ml of a 2% solution of 1,4-benzoquinone in an aqueous-ethanolic medium (50/50) for 8 minutes.

The lock is rinsed with running water and shampooed with an aqueous solution containing 5% of sodium lauryl sulphate.

After rinsing and drying, a black coloured lock is obtained.

The redox potential of the 6-aminoindole determined in a phosphate medium at pH 7 on a vitreous carbon electrode by voltametry is $E_i = 320$ mV.

The redox potential of the 1,4-benzoquinone determined in a phosphate medium at pH 7 by polarography on a mercury electrode relative to the calomel electrode is $E_q = 10$ mV. $\Delta E = 310$ mV.

EXAMPLE 2

The same method as in Example 1 is applied, but a 2.5% solution of 5-aminoindole in an aqueous-ethanolic mixture (80/20) is used instead of the 6-aminoindole.

A chestnut coloured lock is obtained.

The redox potential values determined as in Example 1 are: $E_i = 390$ mV, $E_q = 10$ mV, $\Delta E = 380$ mV.

EXAMPLE 3

The same method as in Example 1 is applied, but a 2.5% solution of 7-aminoindole in solution in an aqueous-ethanolic mixture (80/20) is used instead of the 6-aminoindole.

A deep grey coloured lock is obtained.

The redox potential values determined as in Example 1 are: $E_i = 420$ mV, $E_q = 10$ mV. $\Delta E = 410$ mV.

EXAMPLE 4

The same method as in Example 1 is applied, using a 2.5% solution of 6-N-β-hydroxyethylaminoindole, prepared in accordance with Preparation Example 1 defined above, in an aqueous-ethanolic mixture (80/20) in place of the 6-aminoindole.

A black coloured lock is obtained.

The redox potential values determined as in Example 1 are: $E_i = 265$ mV, $E_q = 10$ mV. $\Delta E = 255$ mV.

EXAMPLE 5

A lock of 1 g of natural hair which is 90% white is impregnated with 5 ml of a 2.5% solution of 4-aminoindole in an aqueous-ethanolic medium (80/20) for 15 minutes.

The lock is rinsed with running water and wrung dry.

This lock is impregnated again using 5 ml of a 2% solution of N-2,6-trichloro-1,4-benzoquinone imine in an aqueous-ethanolic medium (50/50) for 10 minutes.

After having rinsed, washed, rinsed again and then dried, a deep blue coloured lock is obtained.

The redox potential values determined as in Example 1 are: $E_i = 365$ mV, $E_q \geq 180$ mV. $\Delta E \leq 185$ mV.

EXAMPLE 6

The same method as in Example 5 is applied, using a 2.5% solution of 7-aminoindole in an aqueous-ethanolic mixture (80/20) instead of the 4-aminoindole.

A blue-green coloured lock is obtained.

The redox potential values determined as in Example 1 are:

$E_i = 420$ mV, $E_q \geq 180$ mV. $\Delta E \leq 240$ mV.

EXAMPLE 7

The same method as in Example 1 is applied, using a 2% suspension of 1,2-naphthoquinone in a 50/50 aqueous-ethanolic medium instead of the 1,4-benzoquinone.

A purple-violet coloured lock is obtained.

The redox potential values determined as in Example 1 are:

$E_i = 320$ mV, $E_q = -55$ mV. $\Delta E = 375$ mV.

EXAMPLE 8

A lock of 1 g of natural hair which is 90% white is impregnated with 5 ml of a 2.5% solution of 2,3-dimethyl-6-aminoindole in an aqueous-alcoholic medium (80/20) for 15 minutes.

The lock is rinsed with running water and wrung dry. This lock is impregnated again using 5 ml of a 2% suspension of 1,2-naphthoquinone in a 50/50 aqueous-ethanolic medium for 8 minutes.

The lock is rinsed with running water and shampooed using an aqueous solution containing 5% of sodium lauryl sulphate.

After rinsing and drying, a deep grey coloured lock with a purple-violet glint is obtained.

The redox potentials determined as in Example 1 are: $E_i = 145$ mV, $E_q = -55$ mV. $\Delta E = 200$ mV.

EXAMPLE 9

The same method as in Example 1 is applied, but the colour is developed using 2-methyl-1,4-benzoquinone (toluquinone) dissolved in a 50/50 aqueous-alcoholic solution to give a 2% solution.

A medium chestnut coloured lock is obtained.

The redox potential values determined as in Example 1 are:

$E_i = 320$ mV, $E_q = -45$ mV, $\Delta E = 365$ mV.

EXAMPLE 10

The same method as in Example 1 is applied, but the colour is developed using 2-β-hydroxyethylthio-1,4benzoquinone dissolved in a 50/50 aqueous-alcoholic solution to give a 2% solution.

A green coloured lock is obtained.

The redox potential values determined as in Example 1 are:

$E_i = 320$ mV, $E_q = 25$ mV, $\Delta E = 295$ mV.

EXAMPLE 11

The same method as in Example 8 is applied, but the colour is developed using 2-β-hydroxyethylthio-1,4benzoquinone dissolved in a 50/50 aqueous-alcoholic solution to give a 2% solution, replacing the suspension of 1,2-naphthoquinone.

A deep-grey lock is obtained.

The redox potential values determined as in example 1 are:

$E_i = 145$ mV, $E_q = 25$ mV, $\Delta E = 120$ mV.

EXAMPLE 12

The same method as in Example 1 is applied, but the colour is developed using a 2% solution of 2-hydroxymethyl-1,4-benzoquinone in a 50/50 aqueous-ethanolic solution, replacing the 1,4-benzoquinone.

A brown colour is obtained.

The redox potential values determined as in Example 1 are:

$E_i = 320$ mV, $E_q = 5$ mV, $\Delta E = 315$ mV.

EXAMPLE 13

The same method as in Example 1 is applied, but the 6-aminoindole is replaced by 2,3-dimethyl-5-ethyl-6aminoindole.

After developing with 1,4-benzoquinone, a copper red colour is thus obtained.

The redox potential values determined as in Example 1 are:

$E_i = 120$ mV, $E_q = 10$ mV, $\Delta E = 110$ mV.

EXAMPLE 14

The same method as in Example 1 is applied, but the 6-aminoindole is replaced by 2,3-dimethyl-4-methyl-6-aminoindole.

After developing, a brown-russet red colour is thus obtained.

The redox potential values determined as in Example 1 are:

$E_i = 90$ mV, $E_q = 10$ mV, $\Delta E = 80$ mV.

We claim:

1. A process for dyeing keratinous fibers comprising applying to said fibers at least one composition A comprising in a medium suitable for dyeing said fibers at least one aminoindole having the formula

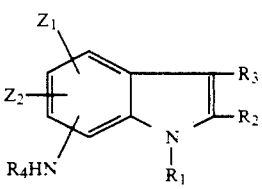

(I)

wherein
$R_1$ represents hydrogen or a linear or branched $C_1$-$C_4$ alkyl,
$R_2$ and $R_3$ represent hydrogen, $C_1$-$C_4$ alkyl, carboxyl or ($C_1$-$C_4$) alkoxycarbonyl,
$R_4$ represents hydrogen, $C_1$-$C_4$ alkyl, $C_1$-$C_4$ hydroxyalkyl, $C_2$-$C_4$ polyhydroxyalkyl, acetyl or $C_1$-$C_6$ aminoalkyl wherein the amine moiety optionally in monosubstituted or disubstituted by a $C_1$-$C_4$ alkyl,
$Z_1$ and $Z_2$, each independently, represent hydrogen, $C_1$-$C_4$ alkyl, halogen or $C_1$-$C_4$ alkoxy,
$NHR_4$ occupying the 4, 5, 6, or 7 positions; and
a salt of said aminoindole, the application of said composition A to said fibers being preceded or followed by the application to said fibers of composition B comprising, in a medium suitable for dyeing said fibers at least one quinone derivative selected from the group consisting of an orthoquinone, a para-benzoquinone, an orthobenzoquinone monoimine, an orthobenzoquinone diimine, a para-benzoquinone monoimine, a para-benzoquinone diimine, a 1,2-napththoquinone, a 1,4- naphthoquinone, an ortho benzoquinone sulphonimide, a para-benzoquinone sulphonamide, an α,ω-alkylene-bis-1,4-benzoquinone, a 1,2-naphthoquinone monoimine, a 1,2-napthoquinone diimine, a 1,4-naphthoquinone monomine and a 1,4-napthoquinone diimine,
the said amino indole and said quinone derivative being chosen such that the difference in the redox potential $E_i$ of said amino indole, determined at pH 7 in a phosphate medium on a vitreous carbon electrode by voltametry, and the redox potential $E_q$ of said quinone derivative, determined at pH 7 in a phosphate medium by polarography on a mercury electrode relative to a saturated calomel electrode is such that $\Delta E = E_i - E_q \leq 470$ mV.

2. The process of claim 1 wherein said aminoindole is selected from the group consisting of 5-aminoindole, 6-aminoindole, 7-aminoindole, 6-N-β-hydroxyethylaminoindole, 6-N-β-hydroxyethylamino-1-methylindole, 6-methylaminoindole, 6-amino-N-methylindole, 6-amino-2-carboxyindole, 4-amino-2,3-dimethylindole, 6-amino2,3-dimethylindole, 7-amino-2,3-dimethylindole, 6-amino-2,3-dimethylindole, 7-amino-2,3-diemethylindole, 6-amino-3-ethyl-2-methylindole, 7-amino-3-ethyl-2-methylindole, 6-amino-3-methylindole, 6-amino-2-methylindole and 6-amino-2-ethoxycarbonylindole, 4-aminoindole, 5-amino-6-methoxy-6-amino 2,3-dimethylindole, 6-amino-5-netgixt-2,3-dimethylindole, 5-amino-N-methylindole, 6-N-(β,γ-dihydroxypropyl)aminoindole, 6-amino 2,3,4,5-tetramethylindole, 6-amino-5-chloro-2,3-dimethylindole, 6-amino-5-ethyl-2,3-dimethylindole, 6-amino-2,3,4-trimethylindole, 4-methylaminoindole, 4-amino-N-methylindole, 6-amino-2,3,7-trimethylindole, 6-amino-2,3,5-trimethylindole, 5-acetylamino-6-methoxy-2,3-demethylindole, 6-amino-4-methylindole, 6-amino-5-methylindole, 4-amino-7-methylindole, 6-amino7-ethyl- 3-methylindole, 6-amino-5,7-dimethylindole, 6-amino-5,7-diethylindole, 7-amino-5-methyl-2-ethoxycarbonylindole, 7-amino-5-ethoxy-2-ethoxycarbonylindole, 7-amino-5-methoxy-2-ethoxycarbonylindole, 7-(4'-dimethylamino-1'-methylbutyl)amino-5-methoxyindole, 7-(4'-dimethylaminobutyl) amino-5-methoxyindole, 6-amino-5-fluoroindole, 6-amino-5-fluoro-1-sec-butylindole, 6-amino-5-fluoro-1-n-propylindole, 6-amino-2-methoxycarbonyl-5-methoxy-N-methylindole, 6-amino-5-methoxy-2-methoxycarbonylindole, 6-amino-5-methoxy-2-ethoxycarbonylindole, 6-amino-5-methoxy-2-carboxyindole and 6-amino-4-methoxy-2-methoxycarbonylindole.

3. The process of claim 1 wherein said quinone derivative has the formula

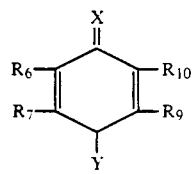

(II)

or the formula

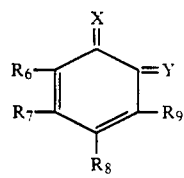

(II')

wherein

X represents oxygen or $NR_{11}$,

Y represents oxygen or $NR_{12}$, $R_{11}$ and $R_{12}$, each independently, represent hydrogen, halogen, $C_1$-$C_4$ alkyl, $C_1$-$C_4$ hydroxyalkyl, $C_1$-$C_4$ alkylsulphonyl or phenylsulphonyl, $R_6$, $R_7$, $R_8$, $R_9$ and $R_{10}$, each independently, represent hydrogen, $C_1$-$C_4$ alkyl, carboxyl, $C_1$-$C_4$ alkylcarbonyl, $C_1$-$C_4$ alkoxycarbonyl, $C_1$-$C_4$ alkoxymethyl, alkylthiomethyl, $C_1$-$C_4$ hydroxy alkylthiomethyl, $C_1$-$C_4$ hydroxyalkylsulphinyl,

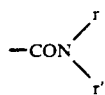

wherein r and r', each independently, represent hydrogen or $C_1$-$C_4$ alkyl, $C_1$-$C_4$ carboxyalkyl, halogen, hydroxyalkyl, amino, aminosubstituted by one or two $C_1$-$C_4$ alkyl or hydroxyalkyl groups, $C_2$-$C_6$ acylamino or $SO_3M$ groups wherein M represents hydrogen, K or Na, sulphoxide, sulphone, sulphonamide, $OZ_1$ wherein $Z_1$ represents hydrogen, $C_1$-$C_4$ alkyl, $C_1$-$C_4$ hydroxyalkyl, $C_1$-$C_4$ carboxylalkyl, phenyl, phenyl substituted by $C_1$-$C_4$ alkoxy or $-SZ_2$ wherein $Z_2$ is $C_1$-$C_4$ alkyl, $C_1$-$C_4$ hydroxyalkyl, $C_2$-$C_4$ dihydroxyalkyl or $C_1$-$C_4$ carboxyalkyl, or $R_6$ and $R_7$ together with the carbon atom to which they are attached, form the cyclic group having the formula

(III)

wherein $R'_1$, $R'_2$, $R'_3$ and $R'_4$ have the meanings indicated for $R_6$, $R_7$, $R_8$, $R_9$ and $R_{10}$ when they do not form rings.

4. The process of claim 1 wherein said quinone is a benzoquinone having the formula

(II)

or the formula

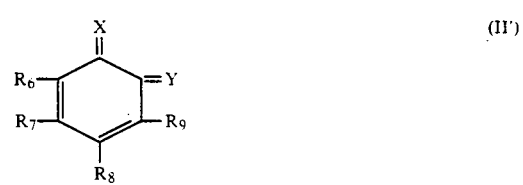

(II')

wherein $R_6$, $R_7$, $R_8$, $R_9$ and $R_{10}$, each independently, represent hydrogen, $C_1$-$C_4$ lower alkyl, $C_1$-$C_4$ lower alkoxy, halogen, $C_2$-$C_6$ acylamino, $SO_3M$ wherein M represents hydrogen, K or Na, $C_1$-$C_4$ alkoxymethyl, carboxy ($C_1$-$C_4$) alkyl, alkoxy ($C_1$-$C_4$) carbonyl, di($C_1$-$C_4$) alkylamino, $OZ_1$ wherein $Z_1$ represents carboxy ($C_1$-$C_4$) alkyl or hydroxy ($C_1$-$C_4$) alkyl, or $SZ_2$ wherein $Z_2$ represents hydroxy ($C_1$-$C_4$) alkyl, dihydroxy ($C_2$-$C_4$) alkyl, carboxy ($C_1$-$C_4$) alkyl or ($C_1$-$C_4$) alkyl, X represents oxygen or $NR_{11}$, Y represents oxygen or $NR_{12}$, and $R_{11}$ and $R_{12}$, each independently, represent hydrogen, halogen, $C_1$-$C_4$ lower alkyl, methylsulphonyl or phenylsulphonyl.

5. The process of claim 4 wherein said quinone derivative is selected from the group consisting of a compound having the formula

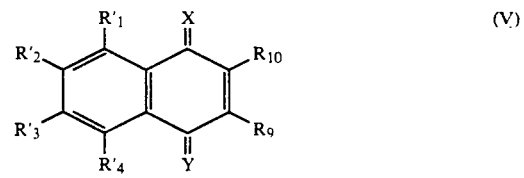

(V)

and a compound having the formula

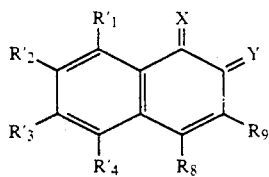

(VI)

wherein $R_8$, $R_9$ and $R_{10}$ have the meanings given in claim 4 and $R'_1$, $R'_2$, $R'_3$, $R'_4$ have the meanings given in claim 4 for $R_6$, $R_7$, $R_8$, $R_9$ and $R_{10}$.

6. The process of claim 1 wherein said quinone derivative is selected from the group consisting of 1,4-benzoquinone, 2-methoxy-1,4-benzoquinone, 2-methyl-1,4-benzoquinone, 2,6-dimethyl-1,4-benzoquinone, 2,3,5-trichloro-6-methyl-1,4-benzoquinone, 2-acetylamino-1,4-benzoquinone, 2-acetylamino-3,5-dimethyl-1,4-benzoquinone, 2-chloro-1,4-benzoquinone, tetrachloro-1,2-benzoquinone, 2,3-dimethoxy 1,4-benzoquinone, 2-β-carboxyethoxy-1,4-benzoquinone, 2-methoxymethyl-1,4-benzoquinone, 2-β-carboxyethoxy-1,4-benzoquinone, 2-mehtoxymethyl-1,4-benzoquinone, 2-β-hydroxymethyl- 1,4-benzoquinone, 2-β-hydroxyethylthio-1,4-benzoquinone, 2,5-bis-β-hydroxyethylthio-1,4-benzoquinone, 2-βγ-dihydroxypropylthio-1,4-benzoquinone, 2-β-carboxyethylthio-1,4-benzoquinone, 2-carboxymethyl-1,4-benzoquinone, 2β-hydroxyethylthio-6-methyl-1,4-benzoquinone, 2-methoxycaronyl-3-methoxy-1,4-benzoquinone, 2-methoxycarbonyl-1,4-benzoquinone, 2-methylthio-1,4-benzoquinone, 2-dimethylamino-1,4-benzoquinone, 2-acetylamino-5-methoxy-1,4-benzoquinone, 2-(β-hydroxyethylthio)-methyl-1,4-benzoquinone, 2-(methylthio)methyl-1,4-benzoquinone, 4,5-dimethoxy-1,2-benzoquinone, 4-methyl-5-chloro-1,2-benzoquinone, 4,5-dimethyl-1,2-benzoquinone, 2,3-demethyl-1,4-benzoquinone, 2-β-hydroxyethoxy-1,4-benzoquinone, N-methylsulphonyl-1,4-benzoquinone monoimine, N-phenylsulphonyl-1,4-benzoquinone monoimine, 1,4-naphthoquinone, 1,2-napththoquinone, 1,2-napthoquinone-4-sulphonic acid, 2,3-dichloro-1,4-napthoquinone, and N-2,6-trichloro-1,4-benzoquinone imine.

7. The process of claim 1 wherein said aminoindole is present in said composition A in an amount ranging from 0.01 to 0.3 mole/liter.

8. The process of claim 1 wherein said quinone derivative is present in said composition B in an amount ranging form 0.005 to 1 mole/liter.

9. The process of claim 1 wherein the pH of said compositions A and B range, independently of one other, from 2 to 10.

10. The process of claim 9 wherein the pH of composition B is acidic.

11. The process of claim 1 wherein said medium suitable for dyeing said fibers is water or a mixture of water and a solvent.

12. The process of claim 1 wherein said medium suitable for dyeing said fibers in an anhydrous solvent medium.

13. The process of claim 1 wherein one or both of said compositions A and B also contain at least one of an anionic, cationic, nonionic or amphoteric surfactant, a thickener, a perfume, a sequestering agent, a film-forming agent, a treatment agent, a dispersing agent, a conditioner, a preservative, an opacifying agent a keratin fiber swelling agent.

14. The process of claim 1 wherein one or both of said compositions A and B also contain another dye selected from a direct dye, an oxidation dye or coupler, or a rapid oxidation dye.

15. The process of claim 1 wherein one or both of said compositions A and B also contain a quinone dye selected from a benzoquinone, a benzoquinone imine, a benzoquinone diimine, a naphthoquinone, a naphthoquinone imine, and a naphthoquinone diimine, said quinone dye having a potential such that $\Delta E$ is greater than 470 mV.

16. A multicompartment kit for use in dyeing keratinous fibers comprising a first compartment housing said composition A defined in claim 1 and a second compartment housing said composition B defined in claim 1.

17. A multicompartment kit for use in dyeing keratinous fibers comprising a first compartment housing said composition A defined in claim 1, a second compartment housing said composition B defined in claim 1, at least one of said compositions A and B comprising an anhydrous solvent medium, and a third compartment containing an aqueous medium to be admixed just before use with the contents of one or the other of said first and second compartments containing said anhydrous solvent medium.

* * * * *